(12) United States Patent
Osipchuk

(10) Patent No.: US 7,429,316 B1
(45) Date of Patent: Sep. 30, 2008

(54) PLANAR PATCH-CLAMP CARTRIDGE WITH INTEGRATED ELECTRODE

(76) Inventor: Yuri Osipchuk, 1271 Swordfish St., Foster City, CA (US) 94404

( * ) Notice: Subject to any disclaimer, the term of this patent is extended or adjusted under 35 U.S.C. 154(b) by 701 days.

(21) Appl. No.: 10/700,652

(22) Filed: Nov. 3, 2003

Related U.S. Application Data

(63) Continuation-in-part of application No. 09/973,388, filed on Oct. 9, 2001, now Pat. No. 6,776,896.

(60) Provisional application No. 60/423,245, filed on Nov. 1, 2002.

(51) Int. Cl.
*G01N 33/487* (2006.01)
(52) U.S. Cl. .................. 204/403.01; 435/288.4
(58) Field of Classification Search ............ 204/403.01; 435/287.1, 288.4
See application file for complete search history.

(56) References Cited

U.S. PATENT DOCUMENTS 5,494,562 A * 2/1996 Maley et al. ................ 257/414
7,201,836 B2 * 4/2007 Vogel et al. ............... 205/777.5
2003/0107386 A1 * 6/2003 Dodgson et al. ............. 324/699

FOREIGN PATENT DOCUMENTS

WO        WO 99/66329    * 12/1999

OTHER PUBLICATIONS

Moussy et al, Anal. Chem. 1994, 66, pp. 674-679.*

* cited by examiner

*Primary Examiner*—Kaj K Olsen
(74) *Attorney, Agent, or Firm*—Antonio R. Durando; Kelvan P. Howard

(57) ABSTRACT

A planar patch-clamp cartridge includes a common ground electrode through a conductive medium reaching into each extracellular chamber. The cartridge is first primed with intracellular solution injected from dispensing tips inserted from above into the intracellular chambers. Then the cartridge is rotated 180 degrees, whereby the intracellular and extracellular chambers assume face-down and face-up positions, respectively. Extracellular solution is then delivered using the same dispensing unit. A plurality of silver tubes engages the intracellular chambers at the end of the rotation to provide electrical conductivity and suction to the intracellular chambers.

12 Claims, 16 Drawing Sheets

PLANAR PATCH-CLAMP CARTRIDGE WITH INTEGRATED ELECTRODE

RELATED APPLICATIONS

This application is based on U.S. Provisional Ser. No. 60/423,245, filed Nov. 1, 2002, and is a continuation-in-part application of Ser. No. 09/973,388 filed Oct. 9, 2001, issued as U.S. Pat. No. 6,776,896.

BACKGROUND OF THE INVENTION

1. Field of the Invention

This invention relates in general to the field of patch-clamp recording and, in particular, to a cartridge system with integrated electrodes suitable for measurements in automated, repeatable, parallel experiments.

2. Description of the Related Art

Conventional voltage clamping techniques used to conduct electrophysiological tests on a membrane assess electrical activity on the membrane by measuring current or voltage changes produced in response to exposure to various test stimuli. Typically, the membrane is pierced with two microelectrodes connected to an amplifier capable of recording current or voltage variations in response to stimuli such as voltage step changes, the application of compounds, or mechanical stimulation.

Similarly, using patch clamping techniques, the membrane potential can be held constant while the current flowing through the membrane is measured to detect ion-channel activity that corresponds to changes in the membrane's conductance. Instead of using sharp microelectrodes to puncture the membrane and penetrate the cell, like in traditional voltage clamping, patch clamping uses a micropipette with a heat-polished tip of about 1 to 5 micron in diameter that is physically sealed to a "patch" on the membrane. The same pipette is used continuously for both current passing and voltage recording. For the most part, patch clamping is used either with a whole-cell or a single-channel mode of operation.

In whole-cell patch clamping, the membrane at the tip of the pipette is ruptured to produce electrical continuity between the electrolyte in the pipette and the interior of the cell. Thus, total membrane current or voltage is measured. In single-channel patch clamping, the integrity of the membrane at the tip of the pipette is preserved. Accordingly, the recorded current is only the current flowing through the patch of the membrane enclosed by the tip of the pipette. Since this area is very small, there is a good chance that only one or a small number of ion channels may be in the membrane patch, and individual ion-channel currents may be recorded.

In both types of patch-clamp techniques, when the tip of the pipette is pressed against the cell membrane, the interior of the pipette is isolated from the extracellular solution by the seal that is formed between the tip of the pipette and the membrane. If the electrical resistance of the seal is sufficiently large, negligible current can leak across the seal and good measurements are obtained. Thus, any leakage of current through the seal is undesirable and the creation of a high-resistance seal (in the order of giga-ohms) is crucial for good results.

The basic design of a patch-clamp recording apparatus includes a chamber filled with an "extracellular" ionic saline solution. Such a chamber could consists simply of a 35 mm Petri dish. A biological membrane or a biological cell that contains ion channels is positioned in the chamber. A patch pipette is fabricated from capillary glass, whereby the tip of the patch has an aperture of one to several microns in diameter. The opposite end of the patch pipette (the pipette "base") is not modified. The patch pipette is filled with an "intracellular" ionic saline solution and a silver wire coated with silver chloride (the "internal electrode") is inserted into the patch pipette through the opening in the base. The wire electrode is positioned such that one end of the wire is in contact with the intracellular saline solution while the opposite end is electrically connected to an electrophysiology headstage. A separate "ground electrode," typically also a silver-chloride coated silver wire, is positioned in the extracellular solution and connected to the electrophysiology amplifier, thus completing the circuit. Electrical current is thus able to flow between the internal electrode and the external electrode via the electrolytes in the intracellular and extracellular saline solutions.

Patch-clamp recording is carried out by positioning the tip of the patch pipette onto the surface of the biological cell (or membrane) and applying suction from the pipette, or other facilitating means, to induce the cell to form a tight seal with the patch pipette. The seal is typically established and monitored by measuring the electrical resistance between the pipette and the cell. An acceptable seal has an electrical resistance on the order of several hundred mega-ohms to several giga-ohms and is often referred to as a giga-seal. Once such a giga-seal has been formed, further suction can be applied to provide whole-cell access to the interior of the cell. This is the most common form of patch-clamp recording. Other variations of patch-clamp recording, such as excised patch, perforated patch, inside-out patch and patch-cramming, are also well known in the art. Once a suitable recording configuration has been obtained, the cell or biological membrane is stimulated and the electrical response is recorded. Common stimuli are also well known in the art.

Planar patch clamping refers to conventional patch clamping wherein multiple cells are recorded at the same time in automatic fashion. Accordingly, planar patch clamping increases the ease, throughput, and reliability of patch-clamp recording. A typical planar patch-clamp apparatus consists of two components with saline-fluid filled chambers separated by a partition with an aperture between each set of chambers. Limiting the description to a single set for ease of discussion, the chambers are typically positioned so that one chamber is above (extracellular chamber) and the other is below (intracellular chamber) the partition. The partition contains a single aperture, approximately one to several microns in diameter, between each set of intracellular and extracellular chambers. Each set of chambers in the planar patch is functionally and structurally substantially the same.

The extracellular chamber is typically filled with extracellular saline solution and a ground electrode is positioned within it, thereby producing a chamber that is functionally equivalent to the extracellular chamber of conventional patch-clamp apparatus. The intracellular chamber is filled with intracellular saline and an internal electrode is similarly placed in it to produce an intracellular chamber that is functionally equivalent to the internal chamber of a patch pipette. The partition between the two chambers is functionally equivalent to the walls of the patch pipette and the aperture in the partition is functionally equivalent to the opening at the tip of a patch pipette. A cell or biological membrane is positioned in the extracellular chamber onto the aperture of the partition. The ground and intracellular electrodes are connected to a ground circuit and a current measurement amplifier, respectively, to complete a circuit.

The electrodes typically consist of a silver wire that has been electrochemically plated with a layer of silver chloride.

During use, both the internal and ground electrode are immersed into their respective fluid solutions and the reaction of silver chloride with chloride ions that are typically present in the solutions provides a suitable conductivity for the performance of the electrodes (i.e., low potential drift and little dependence of the electrode potential on electrical current flowing through the electrode). Since the silver-chloride layer slowly dissolves in the saline solutions, the electrodes have a limited life and require periodic replacement or refurbishment (re-coating with silver chloride).

During the process of planar patch-clamp recording, a giga-ohm seal is formed between the biological membrane and the surface of the partition in the region of each aperture. Suction, or other facilitating means, may be used to rupture the membrane in the aperture, thereby providing whole cell access between the interior of the cell and the intracellular chamber through the aperture in the partition. Electrical current flows between the two chambers through the cell and aperture and is monitored via electrophysiology instrumentation.

Planar patch-clamp for high-throughput screening utilizes multiple-chamber components and disposable planar partitions that are typically attached (bonded or reversibly clamped) to the intracellular component or the extracellular component, or both. The entire assembly of the intracellular component, the partition, and the extracellular component is referred to as a patch-clamp cartridge. Each intracellular component contains a plurality of intracellular chambers (for example 16). Accordingly, each extracellular component also contains a plurality of chambers (such as 16). The partition contains the appropriate number of apertures (e.g., 16) to provide a single aperture for each intracellular chamber. Various cartridge configurations may be desirable for different applications, such as with 96, 384, or 1536 intracellular and extracellular chambers.

It is also possible to use a common electrode for one type of component. For example, a common ground electrode can be used for all the chambers in the extracellular component. In some applications, it may be desirable to have a common chamber as well, rather than discrete chambers, in a given component. For example, a common chamber could be used for the intracellular component with a single electrode for that chamber. Such a common chamber could be coupled to multiple extracellular chambers in the extracellular component via a multiple-apertured partition with a single aperture aligned with each extracellular chamber. In such a case, each of the extracellular chambers would require an independent electrode.

FIG. 1 shows a patch-clamp cartridge 10 consisting of an extracellular component 12, a partition 14, and an intracellular component 16. For planar patch clamping, the internal and ground electrodes (not shown in this figure) are positioned in the intracellular chambers 18 and the extracellular chambers 20, respectively. The electrodes are positioned to contact the solutions in the fluid chambers so that ion current measurement can take place. To be performed automatically, such positioning of the electrodes requires two separate mechanisms, as each electrode is typically positioned on opposite sides of the partition.

This invention is directed at improving the design of patch-clamp cartridges to provide more efficient fluid delivery and electrode operation. It is understood that the concepts described herein are applicable to all types of patch-clamp cartridges used in the art, including those with asymmetrically chambered intracellular and extracellular components.

BRIEF SUMMARY OF THE INVENTION

According to one aspect of the invention, one or both of the electrodes used to carry out planar patch-clamp recording are embedded or integrated into the cartridge, thus reducing the need for automatic positioning of the electrodes. Such simplification increases reliability and decreases the cost of the instrument. A common ground electrode is provided through a conductive medium reaching into each extracellular chamber from the bottom port of the chamber and extending to ground through the bottom of the cartridge's extracellular component. Various conductive media are disclosed, such as a silver layer coated with silver chloride, a silver wire, a silver wire coated with gold, a silver wire coated with a semipermeable layer, and a conductive-gel bridge.

According to another aspect of the invention, a method of solution delivery is disclosed wherein the planar patch-clamp cartridge is first primed with intracellular solution injected into each intracellular chamber from a dispensing tip that is removably inserted into the chamber from above, and then the cartridge is flipped over through a 180-degree arc of rotation. As a result, the intracellular chambers assume a face-down position, while the extracellular chambers on the opposite side are positioned face up. It was found that the intracellular solution is advantageously held in the chambers by surface tension, so that the cartridge can remain so positioned during recording. Because of the corresponding face-up position of the extracellular chambers, the same dispensing tips can also be used to provide extracellular solutions to the extracellular chambers.

This method of solution delivery also enables the use of a novel system of intracellular electrodes. According to the invention, a plurality of silver or silver-lined tubes is aligned with the vertical position assumed by the intracellular chambers at the end of the rotation described above. Thus, they become automatically in contact with the solution in each intracellular chamber to connect it with the recording apparatus.

According to still another aspect of the invention, each extracellular chamber is provided with a sloped wall and the dispensing tip is positioned in contact with the sloped wall prior to the release of solution. Because of the resulting approximately tangential flow of solution along that wall, it was found that the process of exchanging fluids near the bottom of the extracellular chamber is materially improved. Accordingly, the recording conditions of successive measurements are also improved.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DESCRIPTION OF THE PREFERRED EMBODIMENTS OF THE INVENTION

Figure 1:
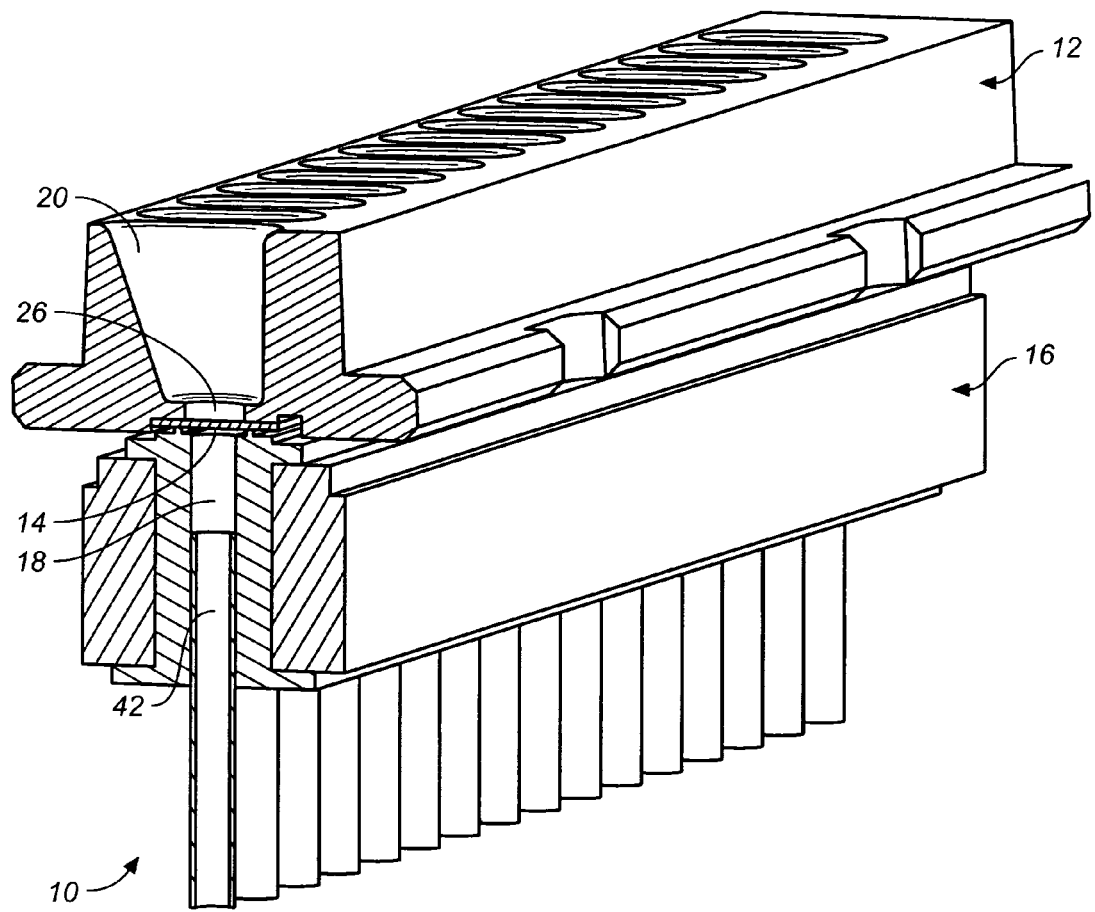
FIG. 1 is a sectioned perspective view of a planar patch-clamp cartridge according to the invention, showing intracellular and extracellular components with respective chambers separated by a planar partition.
Figure 2:
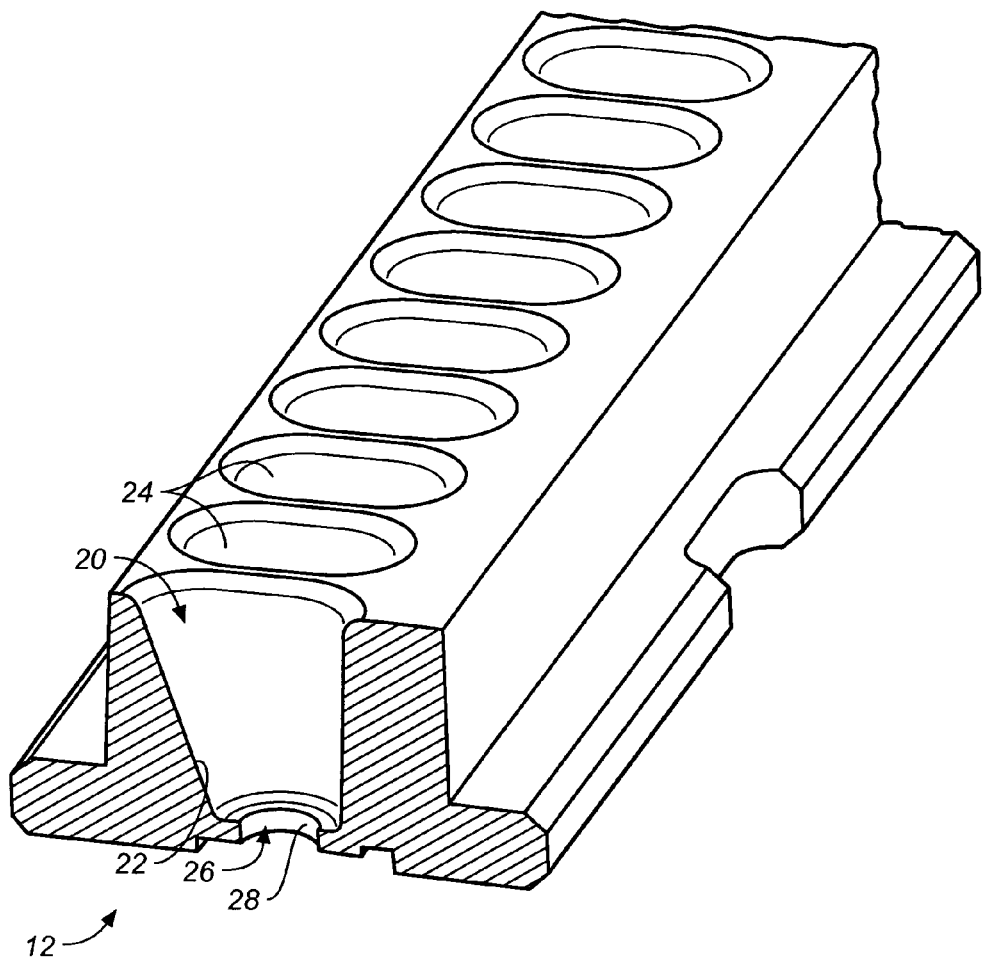
FIG. 2 is a sectioned perspective view of the extracellular component of the cartridge of FIG. 1 showing the interior of a chamber and the associated port to the clamp aperture in the partition (which is not shown).

As used herein, the terms "intracellular" and "extracellular" refer to the two opposite sides of a patch-clamp aperture, typically defined by corresponding chambers adapted to receive fluids and test material. In particular, intracellular and extracellular fluids or solutions are intended to refer to any fluid dispensed to such opposite sides of the aperture, rather than being limited strictly to intracellular and extracellular solutions as these are technically defined in the art. Referring to the figures, wherein the same reference numerals and symbols are used throughout for like parts, FIG. 2 is an exemplary extracellular component 12 of a patch-clamp cartridge 10 according to the invention. The extracellular component 12 contains a number of extracellular chambers 20 (also referred to in the art as wells). Each chamber 20 has a top opening 24 several millimeters in diameter and a bottom port 26. Each chamber has at least one slanted wall 22 positioned at an angle with respect to the vertical axis of the port 26, so as to provide a surface available for contact by the tip of a dispensing unit lowered vertically into the chamber.

Figure 3:
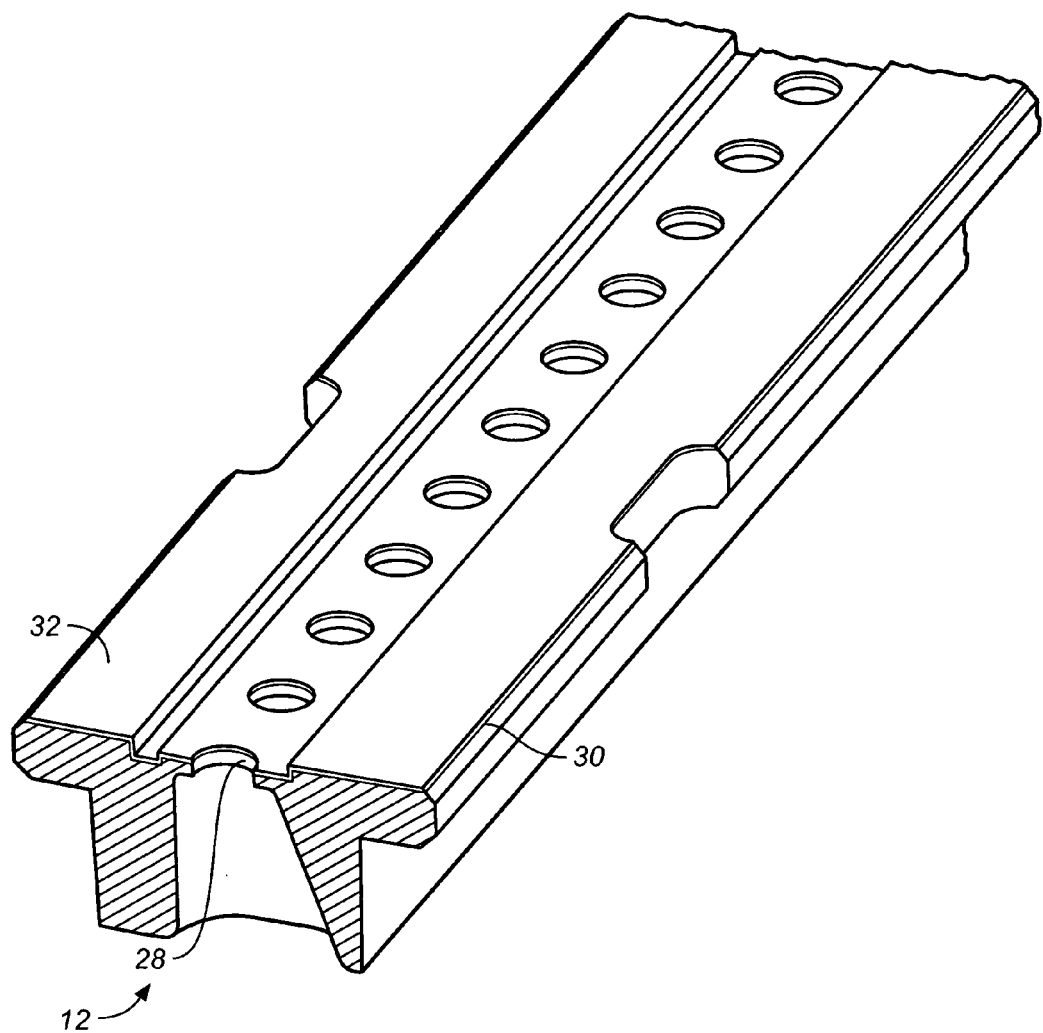
FIG. 3 is a sectioned perspective view of the same extracellular component in up-side-down position to show the silver layer placed on the bottom of the component and extending into the inner walls of the ports.
Figure 4:
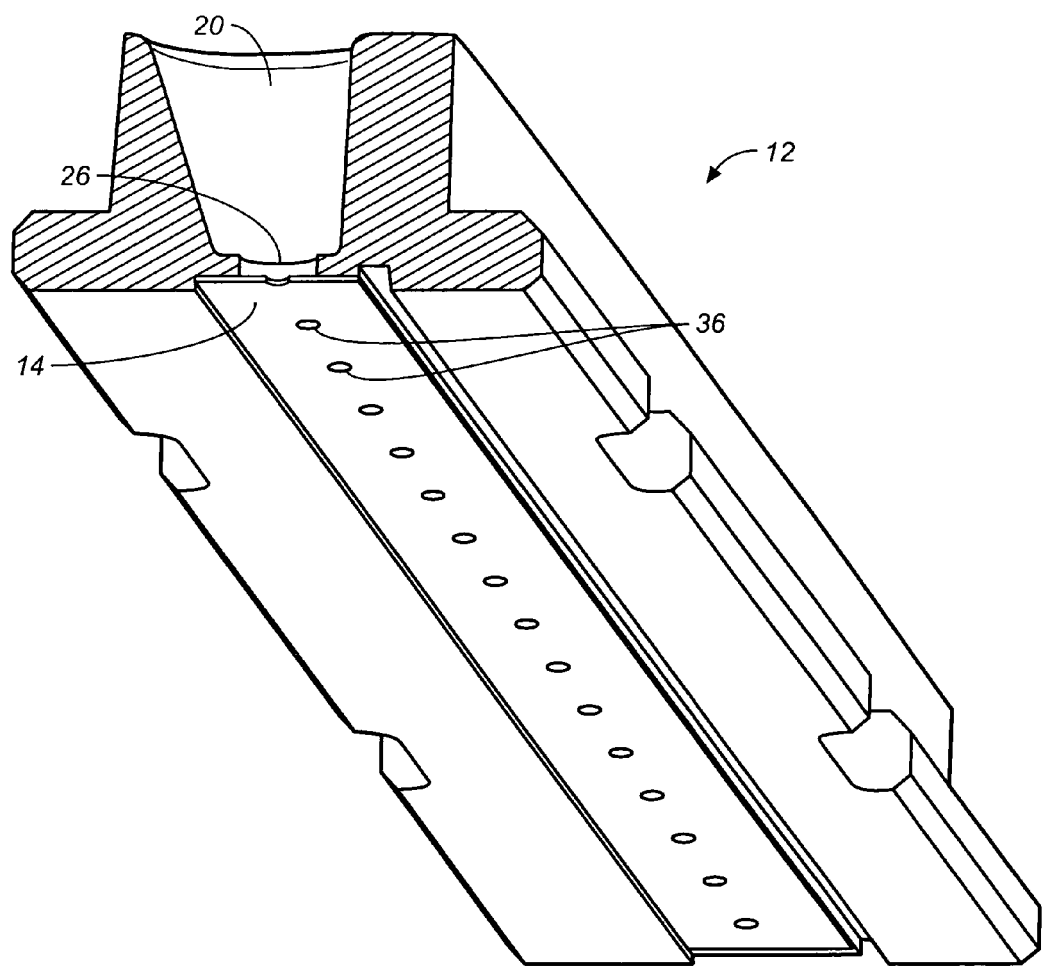
FIG. 4 is a sectioned perspective view of the same extracellular component in right-side-up position illustrating the apertured partition after it is bonded to the surface of the component.
Figure 5:
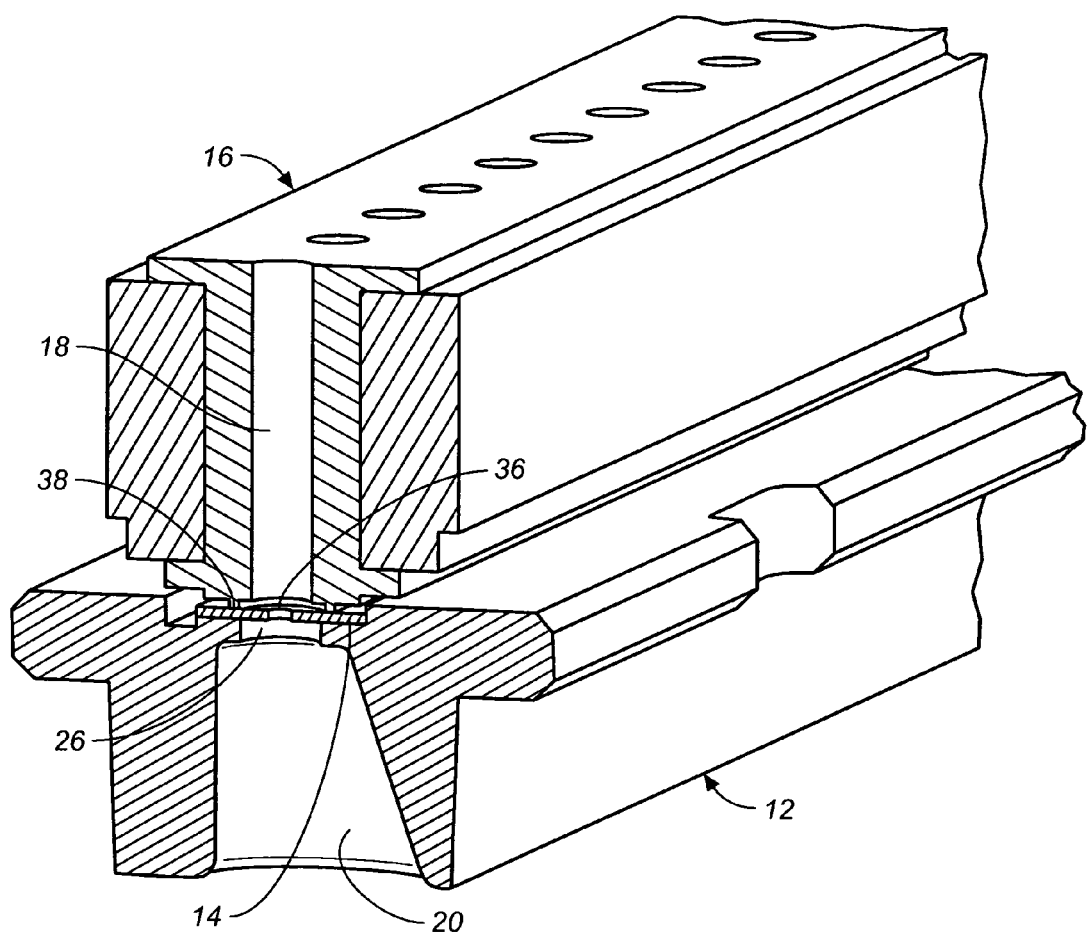
FIG. 5 is a sectioned perspective view of the cartridge of the invention in up-side-down position, as it would appear after assembly in a recording instrument.

The bottom port 26 has an inner wall 28 with an inner diameter of approximately 1.5 mm. According to the invention, a silver electrode layer 32 is deposited (such as by vacuum arc deposition) to extend from the inner wall 28 of the port 26 in each extracellular chamber to the bottom 30 of the extracellular component 12, as illustrated in FIGS. 2 and 3. The inner surface of each chamber 20 is protected from the silver deposition by applying a mask (or plug) to the inside of the chambers during the deposition process. The partition or patch-chip 14 is subsequently bonded to the bottom 30 of the extracellular component 12, as shown in FIG. 5. The partition contains multiple apertures 36, such that a single aperture is aligned with each extracellular chamber 20. Since the silver layer extends from the bottom surface 30 of the component to the inner walls 28 of each chamber port, the solution within each extracellular chamber will be in electrical contact with the silver layer on the surface of the port, which forms one of the electrodes (the ground electrode). The silver layer is coated in conventional manner with a silver-chloride layer (such as by treatment with bleach or by electrochemical reaction).

In one embodiment of the invention, the silver layer in the inner walls of the ports 26 is coated with a silver-chloride layer immediately prior to use. Upon assembly of the cartridge onto the patch-clamp instrument, an appropriate solution containing chloride ions (such as sodium chloride) is then dispensed into each extracellular chamber. Electrical current through the electrode is then used to promote the reaction of silver-chloride deposition. This online coating approach is advantageous because it ensures maximum stability of the ground electrode immediately prior to use. Furthermore, the approach has the additional advantage that it can be performed on a completely assembled cartridge, avoiding the need for additional steps of disassembly and reassembly.

It is known that the silver layer of silver-coated cartridges degrades easily during storage. For example, acidic or basic environments may cause its partial disintegration and a corresponding functional deterioration. Therefore, according to another aspect of the invention, the silver layer is protected by coating it with an inert metal (such as gold) that does not degrade when placed in storage. To that end, gold is electroplated onto the silver layer after the step of silver-layer deposition. The gold layer (or at least a portion thereof) is then removed electrochemically after storage to expose the silver layer, which is subsequently covered with silver chloride immediately prior to use, as detailed above. It should be noted that the concept of on-line silver-chloride deposition and electrode activation is not limited to the cartridge of the invention, but has similar application to any electrode similarly integrated into a patch-clamp cartridge.

In another embodiment of the invention, the silver layer is protected by a coating (such as a thin layer of plastic) that is removed, at least in part, immediately prior to use. Such removal may be carried out through mechanical, chemical, or thermal means.

FIGS. 5-11 illustrate another material improvement derived from the use of a patch-clamp cartridge according to the invention. Because of the small diameter of the apertures 36 in the partition 14 and the narrow channels constituting the intracellular chambers 18, it is difficult to fill both the top and bottom chambers with extracellular and intracellular solutions, respectively, without introducing air bubbles that affect the performance of the instrument. Air bubbles may completely interrupt the electrical connectivity between the top and bottom chambers, or may disrupt the interaction between the biological membrane and the partition. Therefore, a suitable mechanism is needed to load both the extracellular and intracellular chambers with fluid without introducing air bubbles.

The intracellular component 16 typically contains the same number of intracellular chambers 18 as the number of chambers 20 in the extracellular component 12. After assembly of the cartridge, the intracellular component is positioned such that each intracellular chamber is aligned with a single extracellular chamber in the extracellular component, whereby the two chambers are separated by the partition 14. A single aperture 36 in the partition 14 provides electrical continuity between each pair of extracellular and intracellular chambers. The intracellular component preferably consists of an elastomeric material, such as Sylgard or PDMS, embedded in a support frame 40. After alignment, the intracellular component 16 is pressed (or clamped) to the bottom of the extracellular component 12 so that it seals with the partition 14 bonded to the bottom of the extracellular component 12. Special features, such as O-rings 38 molded on the face of the elastomeric intracellular component facilitate the seal. The resulting assembly constitutes a patch-clamp cartridge 10 according to the invention.

The process of assembly of the cartridge 10 is preferably performed starting from the extracellular component 12 held in an inverted position in the recording instrument. The intracellular component 16 is aligned and sealed to the extracellular component, thereby producing a patch-clamp cartridge with vertical intracellular chambers 18 open toward the top. An automatic fluid dispenser unit with individual dispensing tips 44 (FIG. 11) is used to inject a small amount of intracellular saline fluid into each of the intracellular chambers 18. Thus, the intracellular solution contacts the partition 14 and adheres to it and to the surface of the chamber by surface tension.

Figure 6:
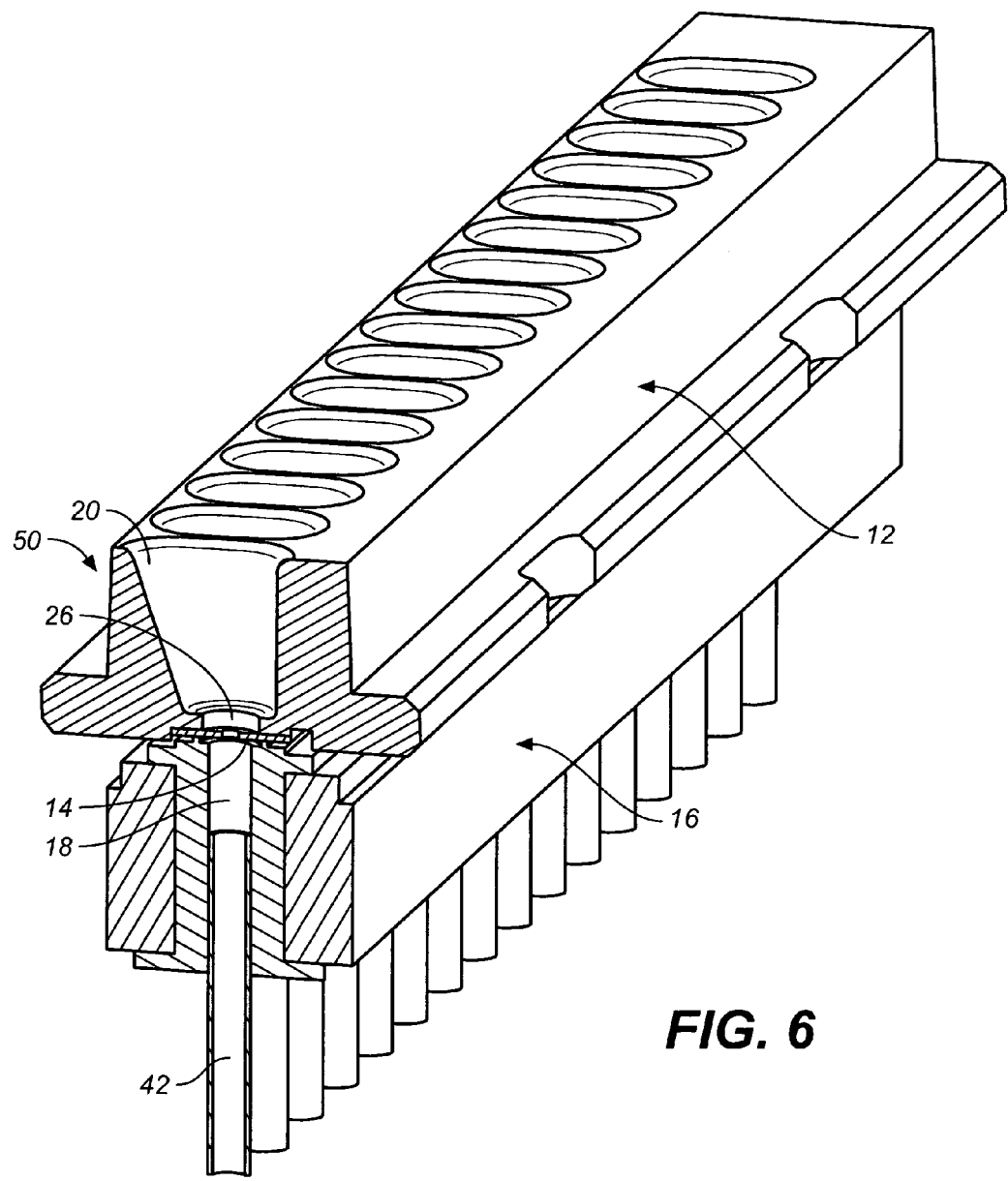
FIG. 6 is a sectioned perspective view of the cartridge of FIG. 5 coupled to a set of intracellular electrodes in the recording instrument after being inverted into its upright recording position through the process illustrated in FIGS. 7-10.

After each chamber in the intracellular component 16 is filled ("primed") with intracellular solution, the entire assembly comprising the extracellular component 12, the bonded partition 14, and the clamped intracellular component 16 (i.e., the patch-clamp cartridge 10) is inverted (flipped) so that the extracellular component 12 is on top, with the top openings 24 of each extracellular chamber 20 facing upwards, as illustrated in FIG. 6. This position is referred to as the recording position. The process of flipping the cartridge is illustrated in sequence in FIGS. 7, 8, 9, and 10.

According to another feature of the invention, silver tubes 42 (which may also consist of another conductive metal, or a non-conductive material partially or totally lined with silver) are permanently affixed to the base 34 of the recording instrument (see FIG. 8) with their respective longitudinal axes perpendicular to the base. The tubes 42 are positioned so that, when the patch-clamp cartridge 10 of the invention is flipped into the recording position, each tube is slidably coupled to a corresponding intracellular chamber 18 in the intracellular component 16, as shown in FIG. 6. The flipping of the cartridge is preferably carried out with a simple rotational motion with a relatively large arc (such as about 200 mm in radius) around an axis of rotation 46 that is offset from the cartridge 10. Such large arc ensures that the motion of the cartridge is approximately linear for a given small radial displacement, so as to ensure a relatively linear travel when the silver bottom tubes 42 are slidably coupled with the chambers 18 of the intracellular component 16.

Figure 11:
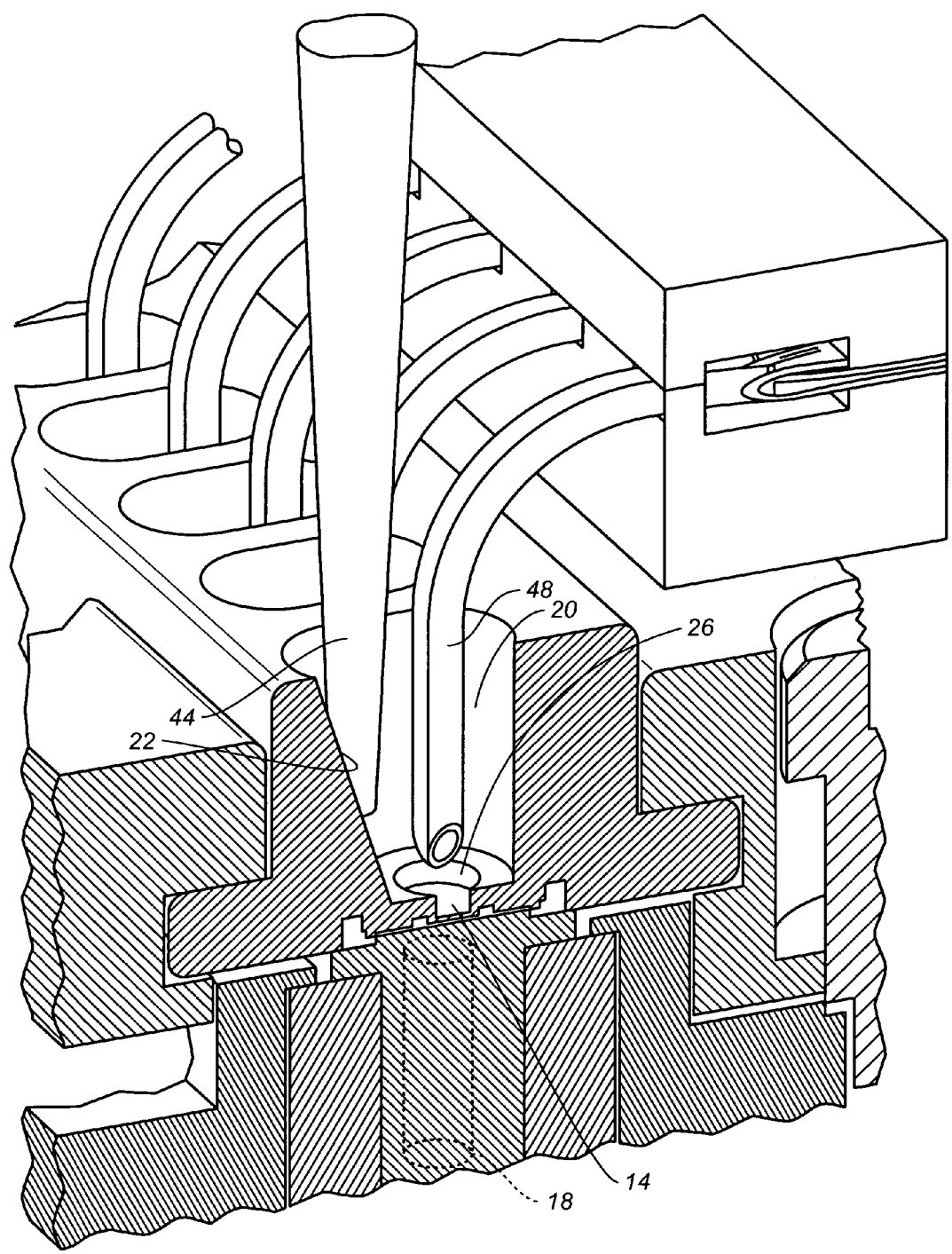
FIG. 11 is a partial sectional view of the cartridge in the recording position showing a dispensing tube in tangential contact with the sloped wall of an extracellular chamber according to the invention.
Figure 12A:
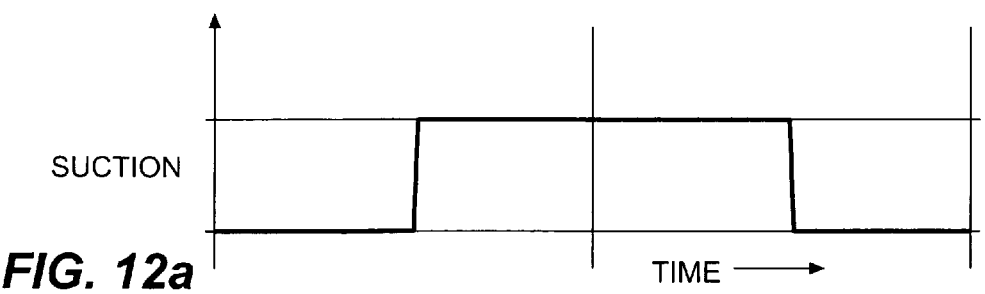
FIG. 12 illustrates suction-versus-time protocols used to gain whole-cell access once a giga-ohm seal has been formed.
Figure 12B:
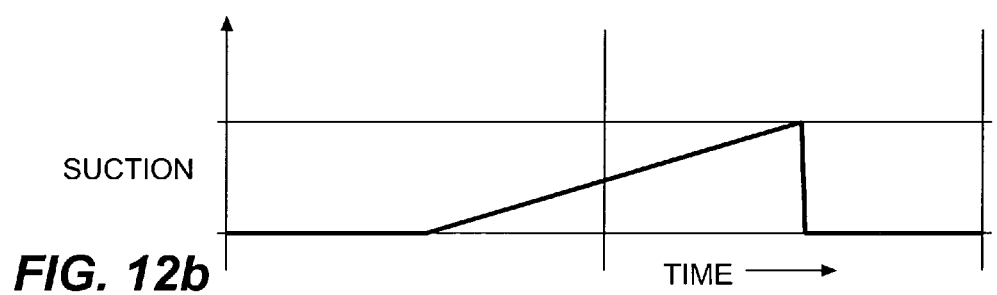
Figure 12C:
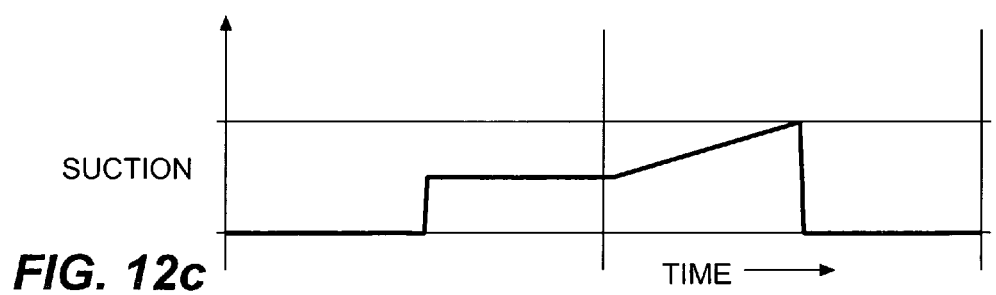
Figure 12D:
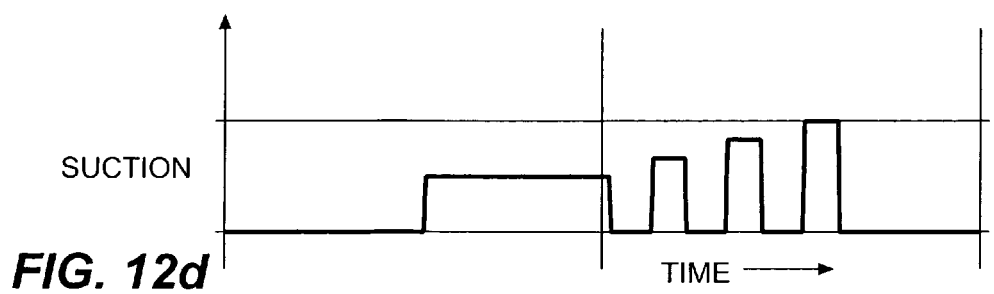

After the intracellular component is seated on the silver tubes 42, each chamber of the extracellular component is filled with extracellular solution by the same automatic fluid dispenser unit used to dispense intracellular fluid, as illustrated in FIG. 11. A suspension of biological membranes (or cells) is delivered by the dispenser, giga-ohm seals are formed, and whole-cell access is obtained in conventional manner. Compounds to be tested are delivered by the dispenser and, after exposure to the biological membrane, they are washed away by washing nozzles 48.

As seen in FIG. 11, for the delivery of solution to the extracellular chambers the dispensing tips 44 are positioned vertically in substantially tangential alignment, preferably in contact, with the sloped walls 22 of the extracellular chambers. The fluid flow that results from this configuration produces a sweeping effect that has been found to facilitate and perfect the process of solution exchange required between the various steps of the recording procedure. Accordingly, the presence of such a sloped wall in the extracellular chambers and the tangential-contact manner of engagement by the dispensing tip 44 are greatly preferred in practicing the invention. In order to ensure such tangential engagement, the tips 44 are preferably pressed against the slanted walls and bent to cause the fluid to flow essentially in parallel to the sloped walls 22.

By flipping the cartridge after filling the intracellular chambers, the same fluid dispenser 44 can be used to fill the extracellular chambers as well. Therefore, although only optional, another advantage of the invention is the ability to use of the same fluid dispenser unit for filling both the intracellular and extracellular chambers.

As mentioned above, in conventional patch-clamp recording a silver wire electrode is inserted into a patch pipette. Suction is then applied to the back (base) of the patch pipette by coupling it to a suction source without affecting the electrode performance. Thus, a desirable advantage could be obtained by integrating the electrode with the means for providing suction, thereby reducing the complexity and cost of the instrument and increasing its reliability.

Figure 7:
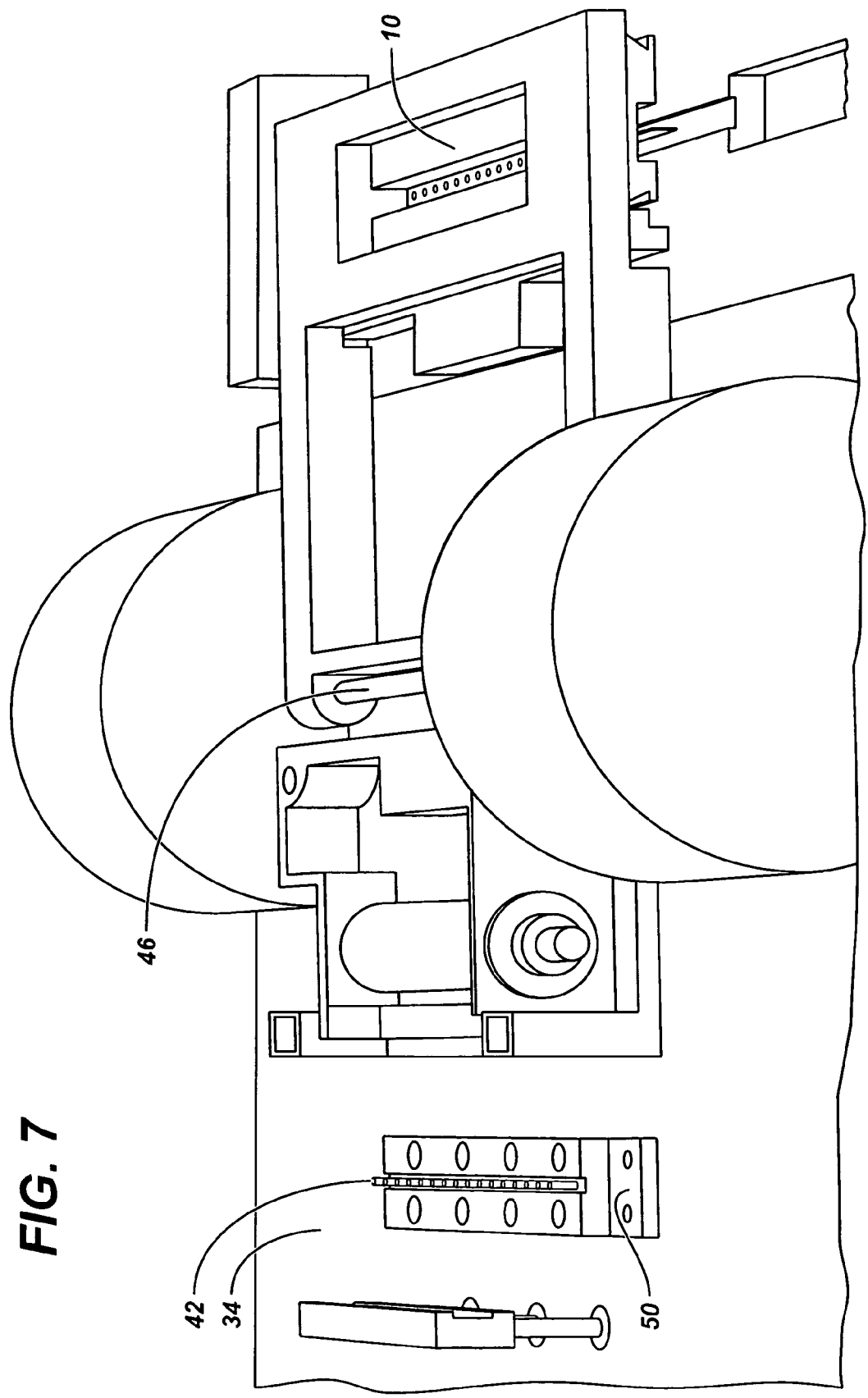
FIG. 7 illustrates the cartridge of the invention loaded on a recording instrument in up-side-down position for the delivery of intracellular solution from a fluid dispensing unit placed above the cartridge.
Figure 8:
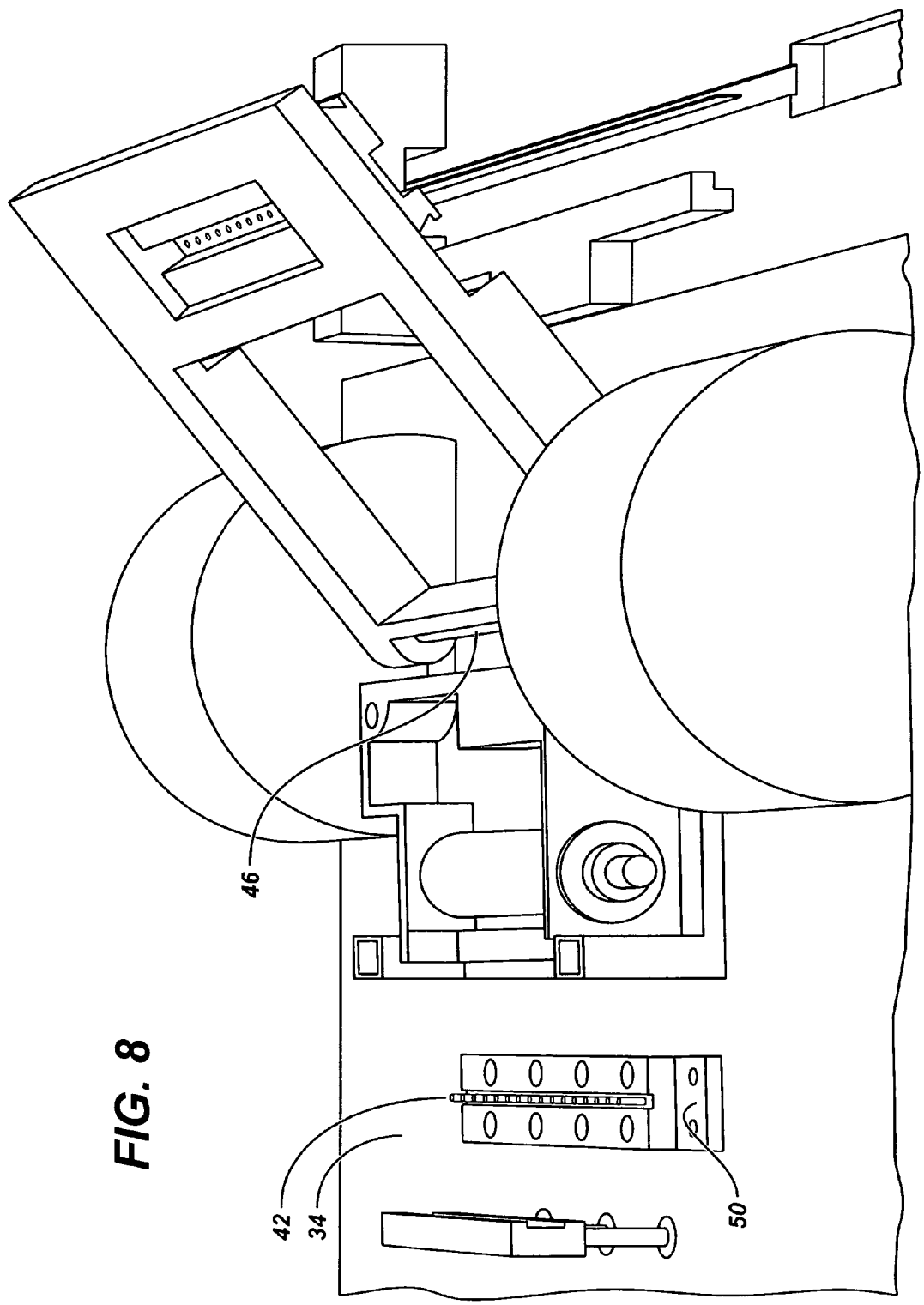
FIG. 8 illustrates the cartridge of the invention being flipped from its initial position to an inverted position through an arc of rotation sufficiently large to produce a substantially linear motion for few degrees of rotation.
Figure 9:
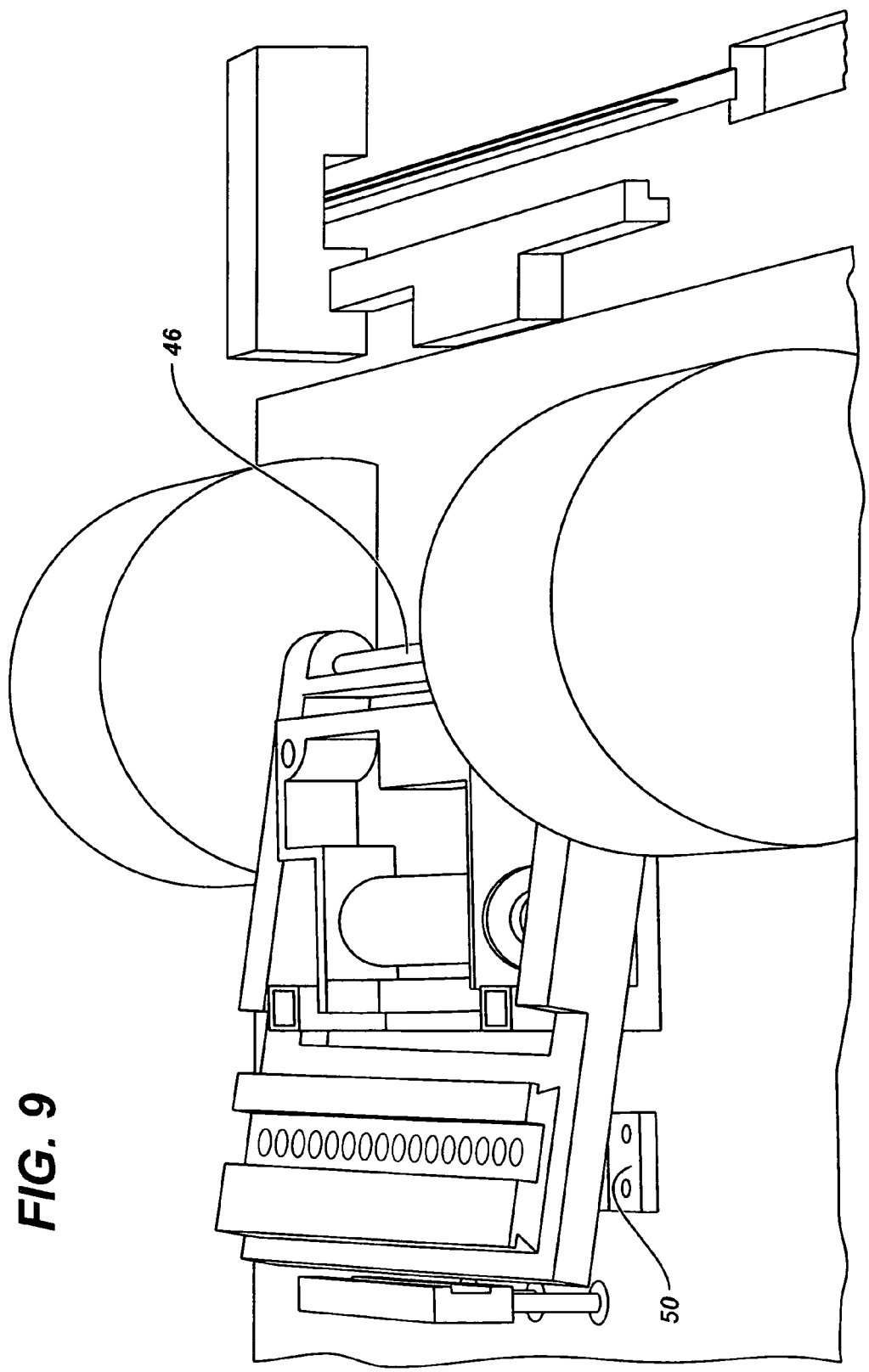
FIG. 9 illustrates the cartridge of the invention as it approaches contact with the set of intracellular silver tubes placed on the base of the recording instrument for engagement with the cartridge's intracellular chambers.
Figure 10:
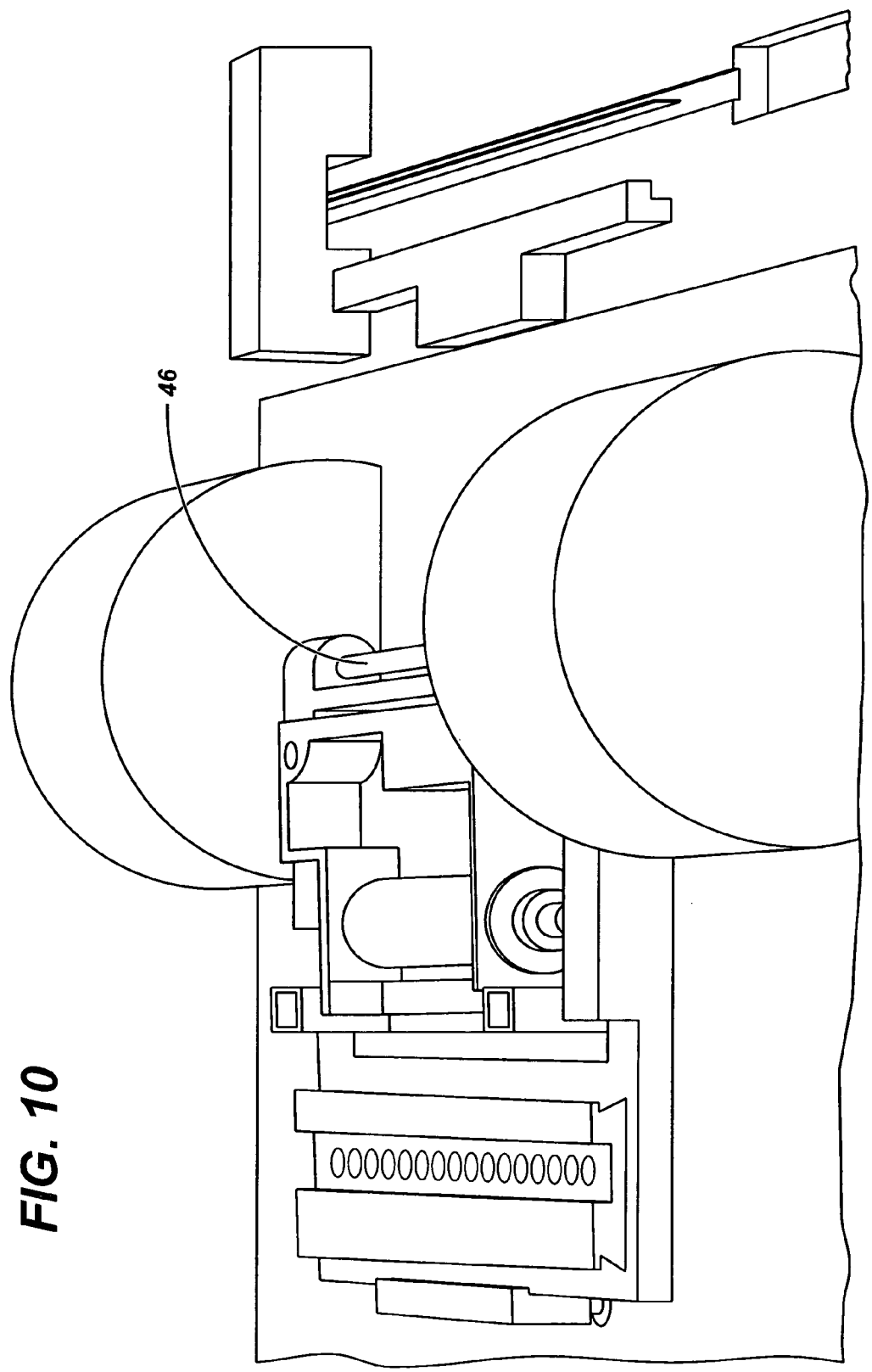
FIG. 10 illustrates the cartridge in its inverted recording position after full engagement of the intracellular silver electrodes.

Accordingly, another aspect of the invention lies in the integration of the intracellular electrodes of the cartridge 10 with the intracellular suction means. As shown in FIG. 7, the silver bottom tubes 42 are connected to a pressure controller 50 that provides the suction needed to position the cell (or the biological membrane) onto the apertures in the partition between the top and bottom chambers. In addition, the suction is used to facilitate the formation of the seal between the biological membrane and the partition. Suction is also used to rupture a portion of the biological membrane to gain whole-cell access. Furthermore, each silver tube 42 is electrically connected to the electrophysiology headstage circuit of the recording instrument and provides the electrical connection between the intracellular solution and the electrophysiology instrumentation. Thus, the silver tubes 42 advantageously serve both as electrical connections to the electrophysiology instrumentation and as pneumatic connections to the pressure controllers.

In addition, the suction applied to the intracellular chambers can be regulated during the course of an experiment based on feedback derived from the instrument and the biological membrane. For example, as disclosed in pending U.S. Pat. No. 6,776,896, a feedback mechanism can be used to regulate suction or positive pressure based on the recorded electrical resistance across the aperture. Additional enhancements can also be made to the suction and pressure feedback system to optimize electrical recording throughout the experiment. Specifically, once a cell has been sealed onto the aperture, a regulated amount of suction can be applied to the cell to rupture the membrane around the aperture and achieve whole-cell access.

Figure 13:
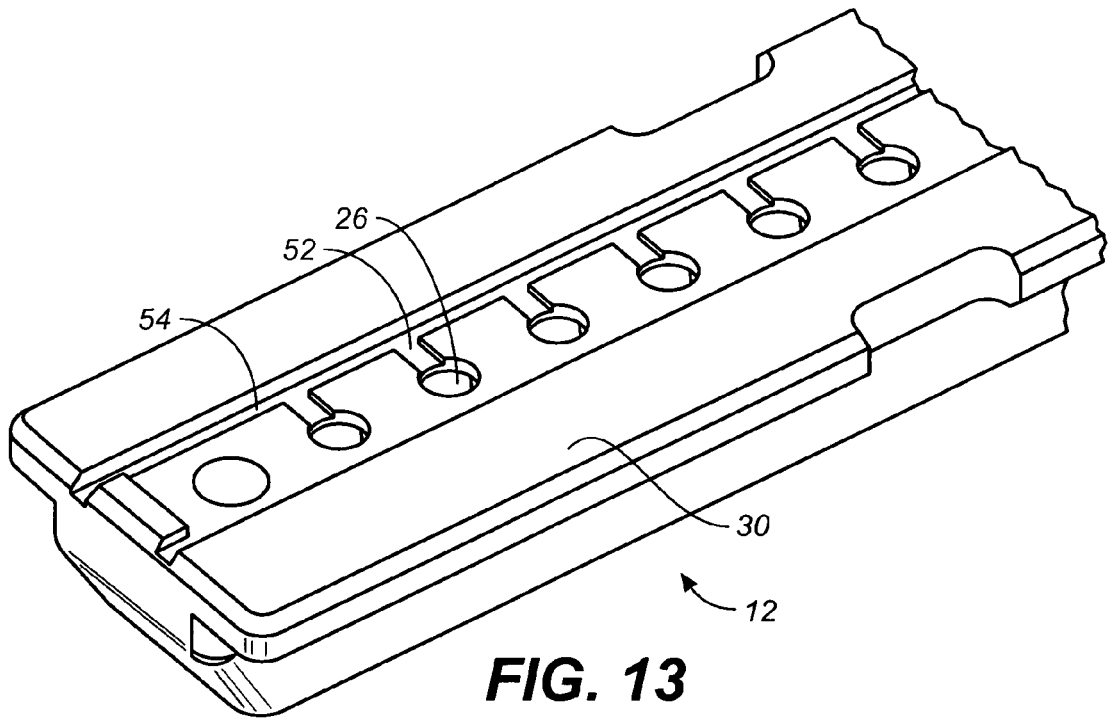
FIG. 13 illustrates channels formed in the extracellular component of the cartridge to receive a conductive-gel bridge connecting the extracellular chambers to ground.

As illustrated in the plots of FIG. 12, suction can be applied according to a number of protocols. For example, it can be applied following (i) a single-step pattern from a low suction pressure to a higher suction pressure (FIG. 12a); or (ii) a ramp protocol where suction is steadily increased to a larger suction level (FIG. 12b); or a combination of (i) and (ii) (FIG. 12c), or a pulsatile suction in either step or ramp fashion (FIG. 12d). While suction is applied, the resistance of the seal is monitored and, once whole-cell access is obtained, suction is returned to a baseline level. Examples of such access protocols are shown in FIG. 13.

After whole-cell access is achieved, the instrument monitors the viability of the cell and the electrical parameters of the membrane. For example, the measured electrical response of the biological membrane to a square voltage step reveals the access resistance, a parameter that is well known in the art. Minimization of access resistance minimizes voltage-clamp errors, also well known in the art. Additional application of suction typically reduces access resistance, but excessive suction may result in loss of the giga-ohm seal. Therefore, it is very desirable to be able to monitor the access resistance precisely and to regulate suction in order to maintain the access resistance within an acceptable range and at the same time avoid rupture of the biological membrane and disruption to the giga-ohm seal. Thus, another enhancement to automated patch-clamp recording lies in the use of computer-controlled regulation of the suction pressures applied during an experiment to minimize access resistance and maximize recording stability.

Algorithms to measure access resistance are well known in the art but require much computation. Thus, monitoring access resistance simultaneously across many apertures (such as the 96, 384, or 1536 apertures present in a parallel planar patch-clamp system) may be very computer intensive and require additional CPU resources. Therefore, another aspect of the invention lies in the utilization of synchronized multiple CPUs to monitor access resistance and the use of an algorithm that is optimized for measuring access resistance while minimizing CPU overhead.

As an alternative embodiment of the invention, the silver layer 32 deposited on the inner walls 28 of the ports 26 and on the bottom surface 30 of the extracellular component to produce a ground electrode (see FIGS. 2 and 3) is replaced with an agar-bridge configuration that prevents direct contact between the silver (or silver chloride) layer and the extracellular saline solution in the extracellular chambers of the extracellular component 12. This is particularly advantageous when harsh storage conditions are present that may degrade the silver layer and negatively affect instrument performance (e.g., poorer electrical response, toxic effects of silver particulates on cells, and impaired ability to form giga-ohm seals). Furthermore, it is well known that an agar bridge is electrically more stable than a conventional silver/silver-chloride electrode when performing solution exchanges with solutions of significantly different ionic composition.

Figure 14:
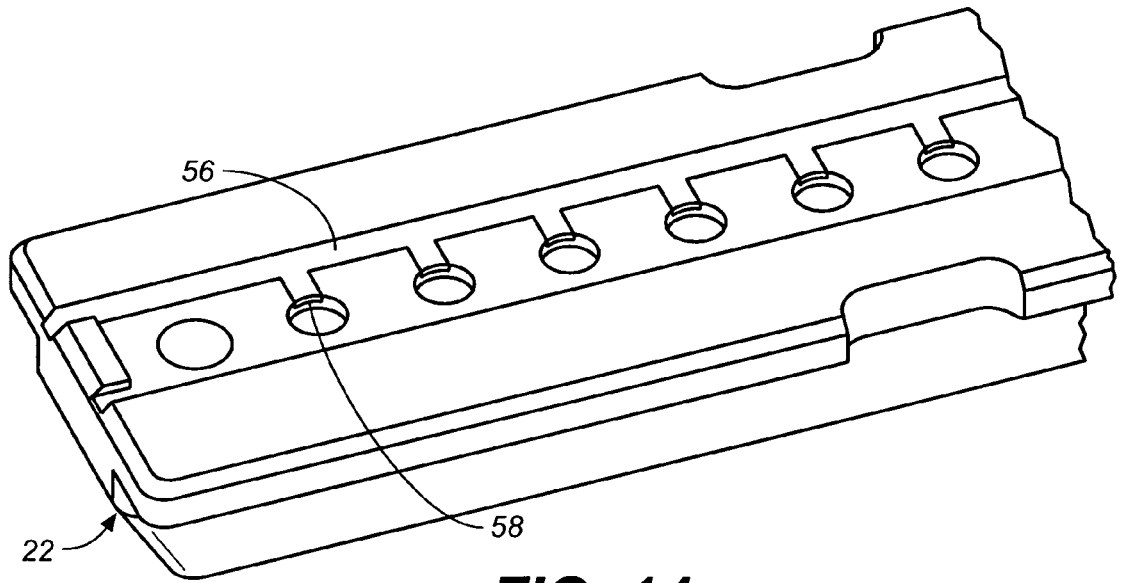
FIG. 14 illustrates the channels of FIG. 13 filled with a conductive-gel.
Figure 15:
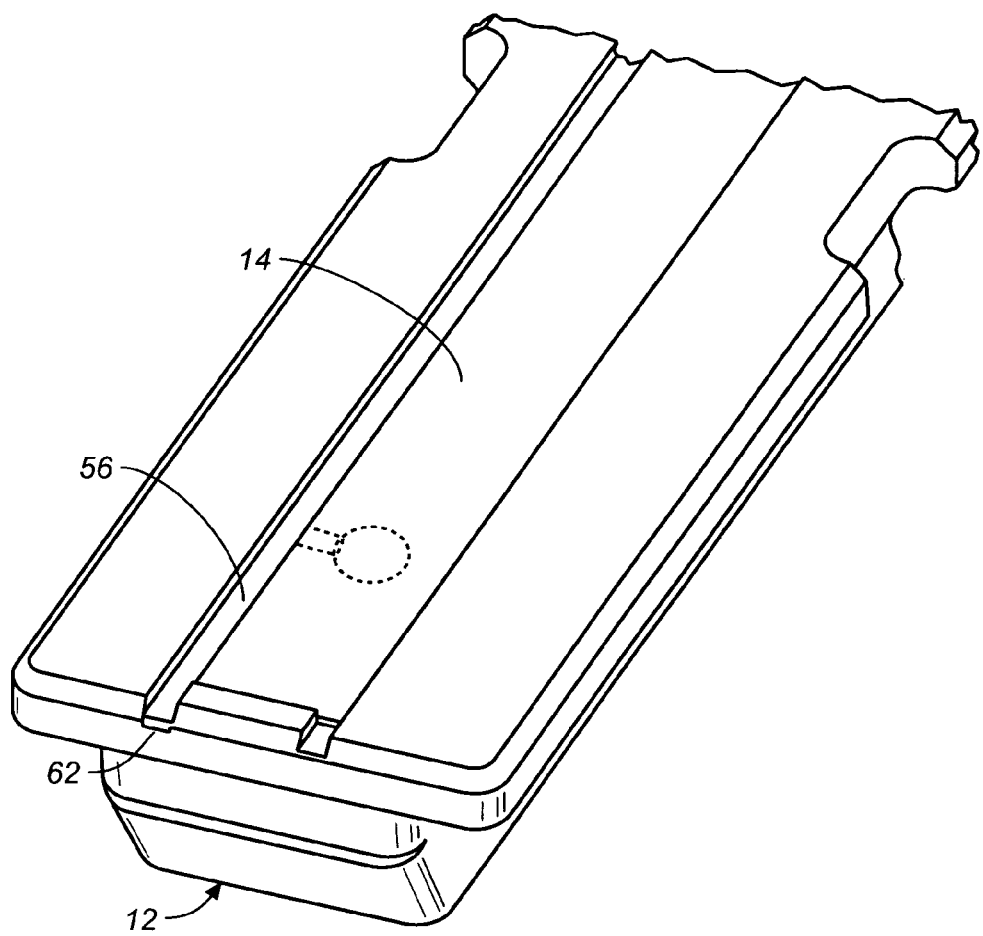
FIG. 15 illustrates the gel bridge of FIG. 14 after the planar patch-clamp partition has been bonded to the extracellular component.

Thus, as illustrated in FIG. 13, the bottom 30 of the extracellular component 12 is modified by adding small transverse channels 52 cut into the surface of the component to reach into the walls 28 of each individual extracellular chamber bottom port 26. A single long channel 54 runs along the main axis of the component to connect the shorter perpendicular channels 52. As illustrated in FIG. 14, these channels are filled with a gel compound 56, for example agarose gel, or polyacrylamide gel, or some other water-based gel-like or porous material, that contains a conductive solution (such as potassium chloride). Accordingly, the gel forms a structure that is in contact with the extracellular solution in each chamber 20.

Figure 16:
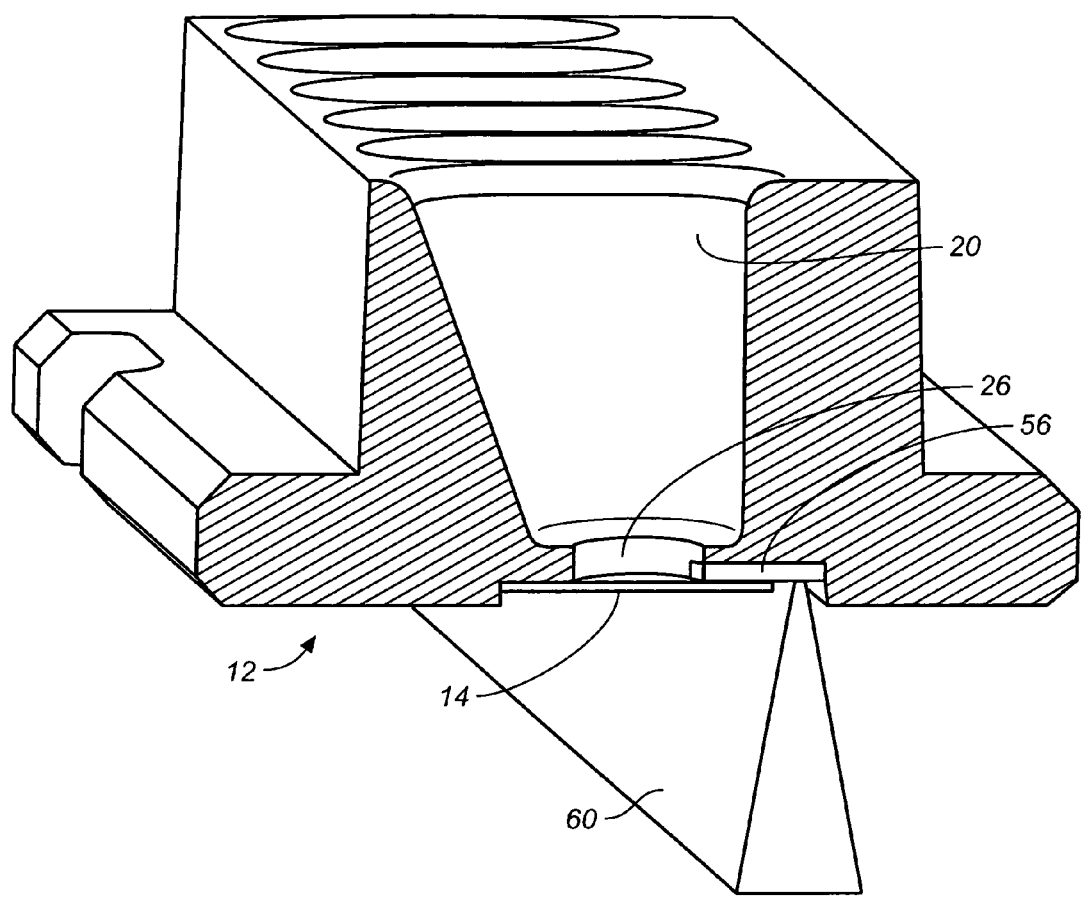
FIG. 16 illustrates an electrode wedge connecting the gel bridge of FIG. 15 to ground.

As shown in FIG. 14, after the gel 56 has solidified in channels 52 and 54, the apertured partition 14 is bonded or clamped to the bottom 30 of the extracellular component 12. As a result of its geometry, a small portion 58 of each transverse channel 52 is left exposed to the port 26, so that the gel 56 in the channel provides a conductive bridge connecting the interior of each extracellular chamber with the gel filling the channel 54. When the extracellular component is assembled with the intracellular component, a wedge-shaped electrode 60 is used to contact the gel in the longitudinal channel 54 through a slot 42, as illustrated in FIG. 16. Such wedge-shaped electrode could consist of an Ag/AgCl electrode incorporated into the frame of the intracellular component. As such, this electrode becomes connected to the inside of each extracellular chamber by the gel bridge, thereby providing the required grounding connection.

Figure 17:
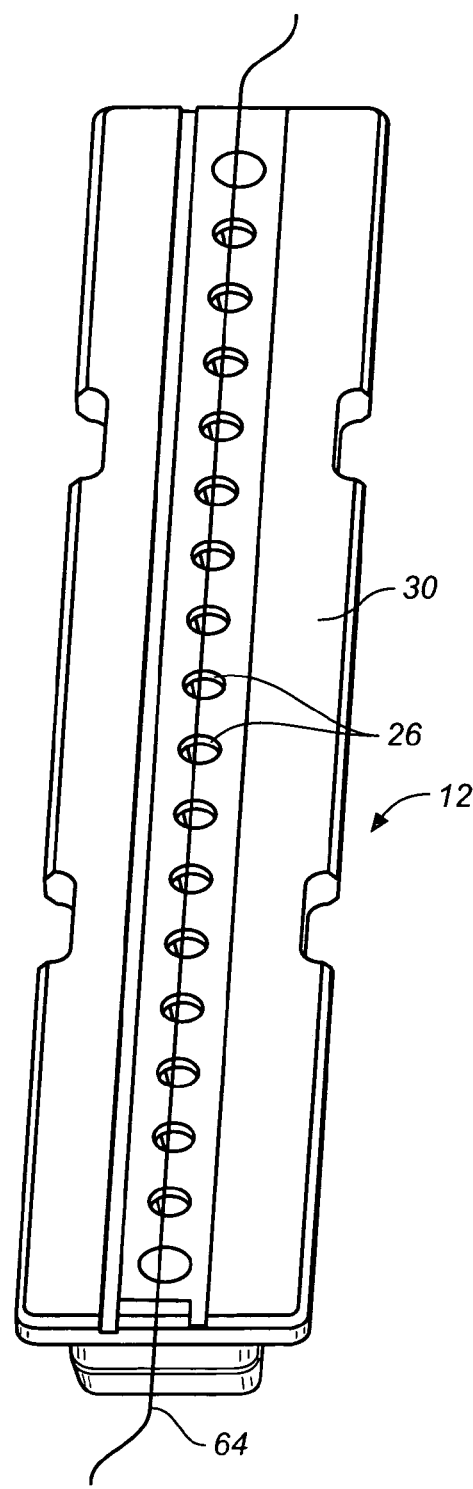
FIG. 17 a bottom view of the extracellular component showing a silver wire running along each aperture in the partition of the invention.

In an alternative embodiment shown in FIG. 17, a metal wire (preferably silver) is used instead of either the silver layer coated onto the surface of the extracellular component (FIG. 3), or the gel-bridge (FIG. 14). Such an embodiment provides the advantage of eliminating the effects of degradation of the silver layer and permits storage of the cartridge (or the extracellular component) in harsher chemical conditions. To that end, a piece of thin silver wire 64 is placed along the entire long axis of the bottom surface 30 of the extracellular component 12, as illustrated in FIG. 17. The wire 64 is positioned such that it passes over each of the access ports 26, but is offset from the center of each port to avoid interference with the partition's apertures. Therefore, a portion of the wire is exposed to the port of each chamber and connection of the extracellular solution with ground can be established through the wire.

The wire 64 may be retained in place using several techniques. For example, electric current can be passed through the wire to heat it and melt the plastic material constituting the extracellular component. This procedure loosely affixes the wire to the plastic. Alternatively, a heated roller wheel could be rolled across the cartridge to deposit the hot wire through a small groove and attach it to the cartridge. To ensure that the wire is completely incorporated into the bottom surface of the extracellular component and that no part is separated, a flat piece of metal (preferably Teflon® coated) may be heated and applied to the plastic bottom surface at a temperature slightly above the plastic's melting temperature. Thus, the heat and pressure force the silver wire into the plastic flush with the cartridge's surface. A hot iron roller could be similarly used. If a groove is left along the wire in the cartridge's surface after such hot treatment, the groove may be filled with the same glue used to bond the partition to the extracellular component.

In yet another embodiment of the invention, the ground electrode is protected by means of a semi-permeable shield. The electrode consists of a wire or thin plate with such a semi-permeable surface between the electrode and the extracellular solution. This semi-permeable surface (in the form of a coating or a membrane) permits ionic current flow from the solution to the metal electrode, but prevents larger particulate molecules (such as silver or silver chloride) from passing into the extracellular saline solution. Therefore, the deterioration of electrode performance is greatly reduced. Such coatings are used, for example, in drug delivery systems and in specialized membranes with differential permeability.

Various changes in the details, steps and components that have been described may be made by those skilled in the art within the principles and scope of the invention herein illustrated and defined in the appended claims. For example, the invention has been described in terms of a cartridge 10 that is assembled prior to delivery of the various fluids required to perform patch-clamp recording. However, all aspects of the invention could be practiced in equivalent manner by providing components with the claimed features and assembling them only as needed during recording. For instance, those skilled in the art know that a minimal amount of solution may be sufficient to perform patch-clamp recording. Therefore, rather than providing an intracellular component or an extracellular component with multiple chambers, it may be sufficient to use one side of the partition 14 without additional structure and to rely only on capillary forces to wet the partition at the aperture sites to establish the patch with a cell and the electrical connection between intracellular and extracellular solutions.

Similarly, the partition could be first wetted by a fluid dispenser and then connected to the appropriate component during the process of recording. For example, the partition coupled to the extracellular component could first be wetted with intracellular solution at a first position and then rotated to meet and be coupled with an intracellular component including electrodes according to the invention (with or without individual intracellular chambers). Alternatively, the partition coupled to the intracellular component could first be wetted or filled with intracellular solution at a first position, rotated to meet and be coupled with electrodes, then coupled with an extracellular component (with or without individual extracellular chambers), which would finally be exposed to extracellular fluid.

It is understood that the invention has also been described in terms of intracellular and extracellular solutions, compartments and chambers, but it is not intended to be so limited. For example, the intracellular and extracellular solutions may be essentially the same, or a different solution may be dispensed to the apertured partition for a particular purpose. Similarly, the rotational displacement of the cartridge may be replaced with the same results by effecting any other motion from a first position, where a solution is dispensed to a first side of the partition, to a second position where another (or the same) solution is dispensed to the opposite side of the partition. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent apparatus and procedures.

I claim:

1. A patch-clamp cartridge comprising:
    an extracellular component including a plurality of separate extracellular chambers formed in an extracellular structure of unitary construction, each extracellular chamber being isolated from other extracellular chambers and sufficiently deep to surround a respective portion of extracellular fluid required for patch-clamp testing;
    an intracellular component including a plurality of separate intracellular chambers formed in an intracellular structure of unitary construction, each intracellular chamber being isolated from other intracellular chambers and corresponding to a respective extracellular chamber;
    an apertured partition sandwiched between the extracellular component and the intracellular component;
    a common extracellular electrode connecting said plurality of extracellular chambers in said extracellular component through a corresponding plurality of extracellular electrode elements exposed to said extracellular chambers through an interface between the partition and the extracellular component; and
    a plurality of individual intracellular electrodes, each of said intracellular electrodes being inserted in a respective intracellular chamber.

2. The cartridge of claim 1, wherein said extracellular electrode includes a metal coating deposited at said interface.

3. The cartridge of claim 2, wherein said metal is silver.

4. The cartridge of claim 3, further including a silver-chloride layer deposited over said silver coating.

5. The cartridge of claim 1, wherein said extracellular electrode includes a metal wire placed at said interface.

6. The cartridge of claim 5, wherein said metal is silver.

7. The cartridge of claim 6, further including a silver-chloride layer deposited over said silver wire.

8. The cartridge of claim 6, further including a semipermeable layer deposited over said silver wire.

9. The cartridge of claim 1, wherein said extracellular electrode includes a conductive gel placed at said interface.

10. A patch-clamp cartridge comprising:
    an apertured partition sandwiched between an extracellular component and an intracellular component; and
    an electrode connecting a plurality of extracellular chambers in said extracellular component through a corresponding plurality of electrode elements exposed to said chambers through an interface between the partition and the extracellular component;
    wherein said electrode includes a silver wire placed at said interface and a gold layer deposited over said silver wire.

11. The cartridge of claim 10, further including a semipermeable layer deposited over said silver wire.

12. The cartridge of claim 10, wherein said extracellular electrode includes a conductive gel placed at said interface.

* * * * *